United States Patent [19]

Kato

[11] Patent Number: 4,467,215
[45] Date of Patent: Aug. 21, 1984

[54] TAPE SURFACE DISCRIMINATING SYSTEM

[75] Inventor: Toshihiro Kato, Kanagawa, Japan

[73] Assignee: Fuji Photo Film Co., Ltd., Kanagawa, Japan

[21] Appl. No.: 331,349

[22] Filed: Dec. 16, 1981

[30] Foreign Application Priority Data

Feb. 24, 1981 [JP] Japan .................................. 56-25034

[51] Int. Cl.³ ............................................. G01B 11/04
[52] U.S. Cl. .................................. 250/571; 250/560; 242/57; 360/74.6
[58] Field of Search .............................. 250/560, 571; 356/384–387; 242/57; 360/74.5, 74.6, 74.7, 76

[56] References Cited

U.S. PATENT DOCUMENTS 2,474,906  7/1949  Meloon ................................ 250/571
3,746,451  7/1973  Croissant et al. ................ 250/560 X Primary Examiner—David C. Nelms
Assistant Examiner—Edward P. Westin
Attorney, Agent, or Firm—Sughrue, Mion, Zinn, Macpeak and Seas

[57] ABSTRACT

A system for discriminating between the front and back surfaces of a tape over the entire length thereof, which comprises a device for discriminating the tape surfaces at least at one end of the tape, and a device for detecting any twisted section at an intermediate point of the moving tape on the basis of a change in the projected area of the tape in the tape width direction.

8 Claims, 12 Drawing Figures

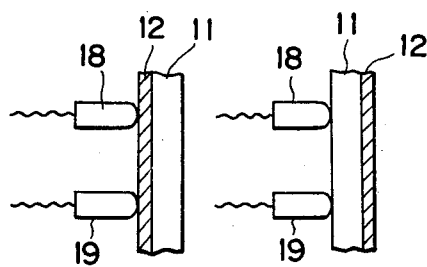
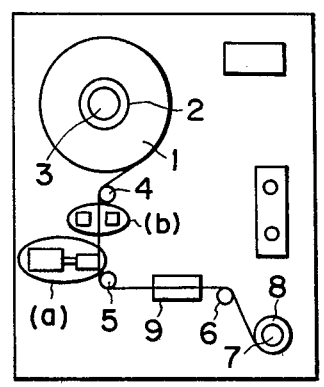
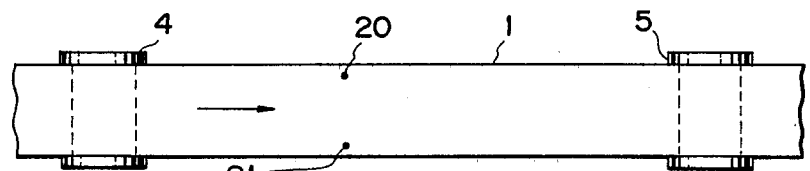
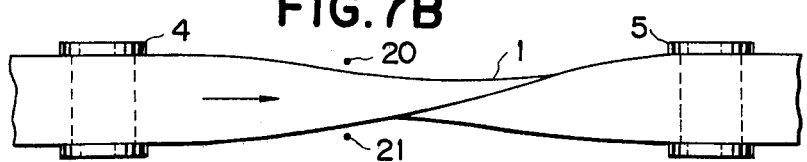
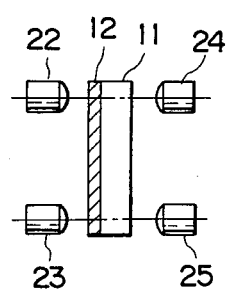
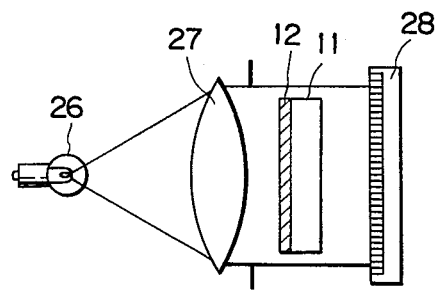

TAPE SURFACE DISCRIMINATING SYSTEM

BACKGROUND OF THE INVENTION

1. Field of the Invention

This invention relates to a system for discriminating the front surface of a tape from the back surface thereof, and more particularly to a system for discriminating between the front and back surfaces of a tape over the entire length thereof in a reliable and easy manner. The term "tape" as used herein means a flexible strip recording medium in the form coiled or wound around a core or delivered from a coiled roll, and broadly embraces magnetic tapes, continuous photographic films and the like.

2. Description of the Prior Art

In general, when preparing a tape as described above, a length 2 to 50 times that of the final product is coiled or wound around a ring-shaped core (hereinafter referred to as the continuous tape hub). Then, a specified length portion of the wound continuous tape is rewound around another ring-shaped core (hereinafter referred to as the product tape hub) suitable for the intended application, and sold in this form. The flexible strip recording medium described above is generally in the form of a tape having a width of about 3 to 51 mm, a length of about 45 to 3,000 m and a thickness of about 3 to 50 μm. Such a recording medium consists of a magnetic or photosensitive film or the like layered on a flexible substrate, and is used for recording and reproducing information. The flexible substrate is, for example, made of a plastic film of, for example, polyethylene terephthalate, polyethylene-2,6-naphthalate, cellulose diacetate, cellulose triacetate, cellulose acetate butyrate, cellulose acetate propionate, polyvinyl chloride, polyvinylidene chloride, polycarbonate, polyimide, and polyamide; paper; paper coated or laminated with paper or an α-polyolefin having from 2 to 10 carbon atoms such as polyethylene, polypropylene or an ethylene-butene copolymer; or a metal foil such as aluminium, copper or tin foil or the like. Typically, such recording media include audio tapes, video tapes, data tapes, 8 mm cine-films and the like.

In general, as shown in FIG. 1, when rewinding the tape from the continuous tape hub to the product tape hub, a continuous tape hub 2 around which a tape 1 has been wound is fitted to an unwind shaft 3. The end of the tape 1 is passed over guide rollers 4, 6, and a length detecting roller 5, and fixed on a product tape hub 8 which engages with a wind-up shaft 7. Motors (not shown) coupled with the unwind shaft 3 and the wind-up shaft 7 respectively are then rotated to move and wind the tape 1 around the product tape hub 8. When the standard length portion of the tape has been wound around the product tape hub 8, the length detecting roller 5 issues a standard length signal to stop the unwind shaft 3 and the wind-up shaft 7. Thereafter, the tape 1 is cut in the standard length by a tape cutter 9 to separate the standard length of tape wound around the product tape hub 8. For this purpose, an apparatus called a winder is generally used.

However, the conventional apparatus of the type described above is disadvantageous as described below. The tape handled is as thin as 3 to 50 μm, and flexible. In addition, the tape width is as small as 3 to 51 mm. Consequently, when the tape moves from the continuous tape hub 2 to the product tape hub 8, it is sometimes twisted turned upside down due to a change in the tape tension or waving movement. If this happens, the tape is wound around the product tape hub 8 in the upside-down condition with the front surface thereof facing back.

If an audio tape is wound around the product tape hub 8 with the front surface thereof facing back and used for recording, the recording head 10 will come into contact with the base layer 11 of the audio tape instead of the magnetic layer 12 thereof, as shown in FIG. 2. Thus, the sound information cannot be recoded on the magnetic layer 12. If a video tape is wound in the inappropriate condition as described above, an image cannot be recorded thereon for the same reason. In addition, it is difficult for the users to recognize during recording whether the sound or image information is actually being recorded. The users become aware of a problem only when reproducing the recorded information, at which time it may be too late for remedial action.

In the past, many methods have been proposed for eliminating the problem described above. For example, for audio tapes or the like, the front and back surfaces of the tape are visually checked at the leading and tail ends thereof when the tape is rewound from the continuous tape hub 2 to the product tape hub 8. Or, as shown in FIG. 3, a recording head 13, a reproducing head 14 and an erasing head 15 are arranged in contact with the tape between the guide roller 4 and the length detecting roller 5 so as to detect the electric input and output signals between the heads and the tape. Alternatively, as shown in FIGS. 4A and 4B, light from a light projector (not shown) is passed through an optical fiber 16 onto a tape surface in contact therewith. In the case of FIG. 4A, light from the light projector further passes through another optical fiber 17 to a light receiver (not shown). In the case of FIG. 4B, light passing through the optical fiber 16 cannot reach the light receiver. Thus the front and back surfaces of the tape are detected on the basis of the light signal between the light projector and the light receiver. Further, it has also been proposed to apply a voltage between two electrodes 18, 19 in contact with the tape and to detect the difference in electrical resistance between the two electrodes, as shown in FIGS. 5A and 5B. However, all of the conventional methods as described above are disadvantageous in that they can only detect the front and back surfaces of the tape at specific sections thereof. These conventional methods cannot reliably detect the front and back surfaces of the tape over the entire length thereof.

More specifically, with the visual check method as described above, it is not possible to recognize the front and back surfaces of the tape when the tape is rewound at a high speed. The method using the recording, reproducing and erasing heads tends to scratch the tape surface due to the friction between the tape and the heads. This conventional method is also disadvantageous in that, when the tape is rewound at a high speed, the electric input and output signals between the heads and the tape become unstable or the tape separates from the heads, causing erroneous judgment regarding the tape surfaces. The conventional optical fiber method described above is disadvantageous in that the moving tape is scratched due to the friction with the optical fibers and, in addition, the tape front and back surfaces cannot be detected correctly if the moving tape separates from the optical fibers. The conventional method based on the electrical resistance described above is also disadvantageous in that the tape suffers from scratches due to the friction with the electrodes and, moreover, the contact force between the electrodes and the tape becomes uneven when the tape moves. This uneven contact force causes erroneous judgment regarding the tape front and back surfaces.

To avoid the problems of the conventional methods described above, the front and back surfaces of the tape are generally investigated at the leading end and/or tail end of the tape only when the tape is stationary. This is done visually or by the optical fiber or electrical resistance method.

However, the conventional methods as described above cannot detect the front and back surfaces of the wound product tape at the central section thereof. With such conventional methods, it sometimes happens that the tape is inappropriately wound around the product tape hub with the front surface thereof facing back if the tape once gets twisted and then returns to the original position when moving from the unwind shaft 3 to the wind-up shaft 7. Such a faulty tape winding also occurs if the continuous tape sent from the previous process has already been turned upside down with the front surface thereof facing down. Further, for thin tapes such as audio and video tapes, it is impossible to discern an upside-down section of the tape even by visually examining the end faces of the wound-up tape with great care.

SUMMARY OF THE INVENTION

The object of the present invention is to provide a system for discriminating between the front and back surfaces of a tape which can eliminate the disadvantages of the conventional methods described above.

Another object of the present invention is to provide a system which can securely discriminate the front surface of a tape from the back surface thereof over the entire length of the tape even if the tape is thin and narrow as described above.

A further object of the present invention is to provide a system for discriminating between the front and back surfaces of a tape which is small in size and simple in construction.

A still further object of the present invention is to provide a system for discriminating between the front and back surfaces of a tape which is inexpensive and easy to maintain.

The above objects are accomplished by the system of the present invention in which the front surface of a tape is discriminated from the back surface thereof at the leading or tail end thereof by the optical fiber or electrical resistance method as described above, and twisting of the tape at an intermediate section thereof is monitored and detected by a device for detecting a change in the projected dimension of the tape width which occurs when the tape is turned upside down.

BRIEF DESCRIPTION OF THE DRAWINGS

FIGS. 3, 4A, 4B, 5A and 5B are explanatory views showing the conventional discrimination systems for the front and back surfaces of a tape, FIG. 6 is a front view showing part of a system according to an embodiment of the present invention, FIGS. 7A, 7B and 8 are explanatory views showing details of FIG. 6, and FIG. 9 is an explanatory view showing part of a system according to another embodiment of the present invention.

DESCRIPTION OF THE PREFERRED EMBODIMENTS

Figure 1:
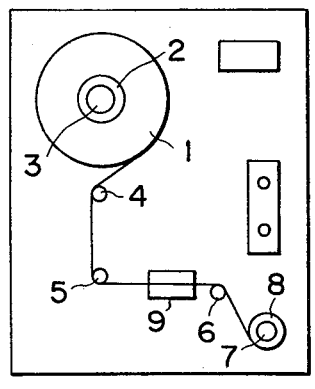
FIG. 1 is a front view of a winder.
Figure 2:
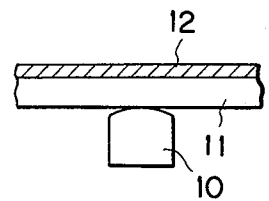
FIG. 2 is an explanatory view showing how a magnetic tape is used.
Figure 3:
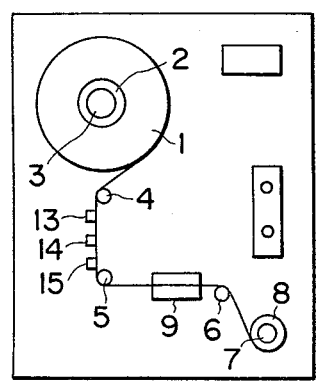
Figure 4A:
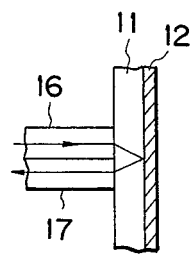
Figure 4B:
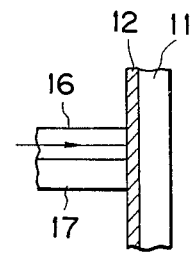

Now the present invention will be described in detail with reference to the drawing.

Referring to FIG. 6 showing an embodiment of the present invention, reference character (a) designates a detecting section based on the optical fiber or electrical resistance method described above, and (b) a detecting section for detecting a change in the projected dimension of the tape width. The detecting section (b) for detecting a change in the projected dimension of the tape width will be described in detail with reference to FIGS. 7A, 7B and 8.

FIG. 7A shows the condition of the tape when it is moving normally. FIG. 7B shows the condition of the tape when it is twisted and moving in the twisted state between a guide roller 4 and a length detecting roller 5. Between the guide roller 4 and the length detecting roller 5, two pairs of light projectors 22, 23 and light receivers 24, 25 are arranged so that respective light projectors 22, 23 on one side of the tape are opposed to the corresponding light receivers 24, 25 on the other side of the tape, as shown in FIG. 8. The light projectors 22, 23 and light receivers 24, 25 are positioned so that their optical axes pass through points 20, 21 at the edge sections in the width direction of the tape. When the tape 1 is moving normally as shown in FIG. 7A, the light beams emitted from the light projectors 22 and 23 are interrupted by the tape 1 and do not reach the light receivers 24 and 25. When the tape 1 is twisted and its front and back surfaces are turned upside down as shown in FIG. 7B, the light beams emitted from the light projector 22 and/or light projector 23 reach the light receiver 24 and/or light receiver 25 without being interrupted by the tape 1. Therefore, the twisting of the tape 1 can be detected easily from the light signal.

For example, light emitting diodes can be used as the light projectors, and photo transistors can be used as the light receivers. It is also possible to use tungsten-filament lamps and solar batteries as the light projectors and light receivers. Instead of using two pairs of light projectors and light receivers, it is also possible to make the light coming out of a lamp 26 parallel by a lens 27, and to detect the shadow of the magnetic tape 11, 12 by a linear array 28. In this case, the twisted section of the tape is detected from the change in the amount of light received by the linear array 28.

The device for discriminating between the front and back surfaces of the intermediate section of the tape wound around the product tape hub should be arranged for each winder. As for the device for detecting the front and back surfaces of the tape at the leading or tail end thereof, if there is a point where many tapes to be wound around the product tape hubs gather, it is sufficient to install one such device at such a point. Such an arrangement reduces the equipment cost and facilitates the maintenance of the equipment.

The system of the present invention can also be used to discriminate the front and back surfaces of webs of magnetic tape, cine-film, photographic film or the like when these are wound up after the slitting process.

I claim:

1. A system for discriminating between the front and back surfaces of a tape having a given width comprising; first means for discriminating the front and back surfaces of a tape at least at one end thereof, and second means for detecting any section of the tape twisted at intermediate sections of the moving tape on the basis of a change in an actual width of the tape created when said tape twists such that its actual width is different from said given width.

2. A system for discriminating between the front and back surfaces of a tape as defined in claim 1 wherein said first means is a device in which a light beam is emitted from a light projector onto the tape, the light beam reflected from the tape is received by a light receiver, and the difference between the amounts of the light reflected from the front and back surfaces of the tape is discriminated.

3. A system for discriminating between the front and back surfaces of a tape as defined in claim 1 wherein said first means is a device discriminating the difference between the electrical resistance values of the front and back surfaces of the tape.

4. A system for discriminating between the front and back surfaces of a tape as defined in any of claims 1, 2 or 3 wherein said second means is a device in which two light projectors are opposed in paired relation to two light receivers across the tape with the optical axes of the paired light projectors and light receivers passing through the tape at both edges thereof, and the light beam or beams reaching one or both of the light receivers are detected to detect any tape section twisted.

5. A system for discriminating between the front and back surfaces of a tape as defined in any of claims 1, 2 or 3 wherein said second means is a device in which the light coming out of a lamp is made parallel by a lens and projected toward the tape onto a linear array which detects the shadow of the tape.

6. A system for discriminating between the front and back surfaces of a tape as defined in claim 5 wherein said tape is a recording or reproducing medium.

7. A system for discriminating between the front and back surfaces of a tape as defined in any of claims 1, 2 or 3 wherein said tape is a recording or reproducing medium.

8. A system for discriminating between the front and back surfaces of a tape as defined in claim 4 wherein said tape is a recording or reproducing medium.

* * * * *